United States Patent [19]
Kakuda et al.

[11] Patent Number: 5,501,866
[45] Date of Patent: Mar. 26, 1996

[54] PRODUCT AND METHOD FOR INHIBITING CAFFEINE STIMULATION WITH THEANINE

[75] Inventors: Takami Kakuda; Takanobu Matsuura; Yuko Sagesaka; Toshio Kawasaki, all of Tokyo, Japan

[73] Assignee: Ito En, Ltd., Tokyo, Japan

[21] Appl. No.: 408,170

[22] Filed: Mar. 21, 1995

Related U.S. Application Data

[62] Division of Ser. No. 117,814, Sep. 8, 1993, abandoned.

[30] Foreign Application Priority Data

Dec. 2, 1990 [JP] Japan .................... 2-414871

[51] Int. Cl.$^6$ .................... A23F 3/00; A23F 5/00
[52] U.S. Cl. .................... 426/594; 426/595; 426/596; 426/597; 426/656
[58] Field of Search .................... 426/594, 595, 426/596, 597, 656

[56] References Cited

FOREIGN PATENT DOCUMENTS

| | | | |
|---|---|---|---|
| 46-10920 | 3/1971 | Japan | 426/597 |
| 59-41692 | 10/1984 | Japan . | |
| 59-41377 | 10/1984 | Japan . | |
| 59-41378 | 10/1984 | Japan . | |
| 59-46576 | 11/1984 | Japan . | |

OTHER PUBLICATIONS

Stahl, W. The Chemistry of tea and tea manufacturing, Mc Cormick & Co., Inc, Baltimore Maryland. pp. 201–219. No publishing date is available.

*Primary Examiner*—Helen Pratt
*Attorney, Agent, or Firm*—Lowe, Price, LeBlanc & Becker

[57] ABSTRACT

The caffeine stimulation inhibitor that inhibits stimulation by combining the use of theanine extracted from tea leaves and/or a substance having theanine for its major active ingredient which is produced by extracting tea leaves with a solvent such as water, hot water or ethanol, chemical synthesis, microbial fermentation or plant tissue culturing. These active ingredients are able to inhibit the stimulatory action of caffeine without degrading the quality, such as the flavor and aroma, of caffeine-containing beverages and foods, allowing persons hypersensitive to caffeine to consume caffeine-containing beverages and foods without worry over its effects.

11 Claims, 2 Drawing Sheets

PRODUCT AND METHOD FOR INHIBITING CAFFEINE STIMULATION WITH THEANINE

This application is a division of application Ser. No. 08/117,814 filed Sep. 8, 1993, now abandoned.

BACKGROUND OF THE INVENTION

1. Field of the Invention

The present invention relates to a caffeine stimulation inhibitor, and more particularly, to the combined use of theanine extracted from tea leaves and/or a substance having theanine for its main active ingredient.

2. Description of the Prior Art

The caffeine contained in tea, coffee and so forth is removed by physical or chemical techniques for people who are hypersensitive to caffeine.

Known examples of the prior art include a water extraction process (Japanese Patent Publication Kokoku No. 59-41692, Japanese Patent Publication Kokoku No. 59-45576), an organic solvent extraction process (Japanese Patent Publication Kokoku No. 59-41378), a supercritical gas extraction process (Japanese Patent Publication Kokoku No. 59-41377) and a process wherein caffeine is physically removed by adsorption by passage over a liquid chromatography column filled with a styrene-divinyl-benzene polymer.

However, in the water extraction process, tannin and polyphenol are decomposed resulting in significant deterioration of color and flavor, while in the organic solvent extraction process, ingredients that compose flavor in addition to caffeine are removed particularly resulting in deterioration of flavor. In addition, in the supercritical gas extraction process, chlorophyll and tannins are decomposed due to the extremely high pressure resulting in a decrease in the product value of the raw beans, while in the adsorption process as well, ingredients such as tannin and amino acids other than caffeine are also removed resulting in deterioration of flavor and aroma.

On the other hand, rather than employing processes involving removal of caffeine as in the processes described above, a method using an existing substance contained in natural substances as a caffeine antagonist, wherein said substance is added to beverages and foods to inhibit the stimulatory action of caffeine, is not yet known.

SUMMARY OF THE INVENTION

The object of the present invention is to provide a caffeine stimulation inhibitor that is able to inhibit the stimulatory action of caffeine without deteriorating the quality, such as the flavor and aroma, of the caffeine-containing beverage or food.

In order to accomplish the above-mentioned objective, the present invention provides a caffeine stimulation inhibitor, or antagonist, that can be added to caffeine-containing beverages and foods, which is a caffeine stimulation inhibitor having theanine and/or a theanine-containing substance as its active ingredient, wherein said theanine or theanine-containing substance is produced by extraction of tea leaves with a solvent such as water, hot water or ethanol, chemical synthesis, microbial fermentation, plant tissue culturing or other processes.

Theanine and/or compositions having theanine for their active ingredient can be obtained from tea leaves widely distributed throughout nature. This natural ingredient demonstrates stimulation inhibitory action by acting as an antagonist of the action of caffeine.

DETAILED DESCRIPTION OF THE INVENTION

Figure 1:
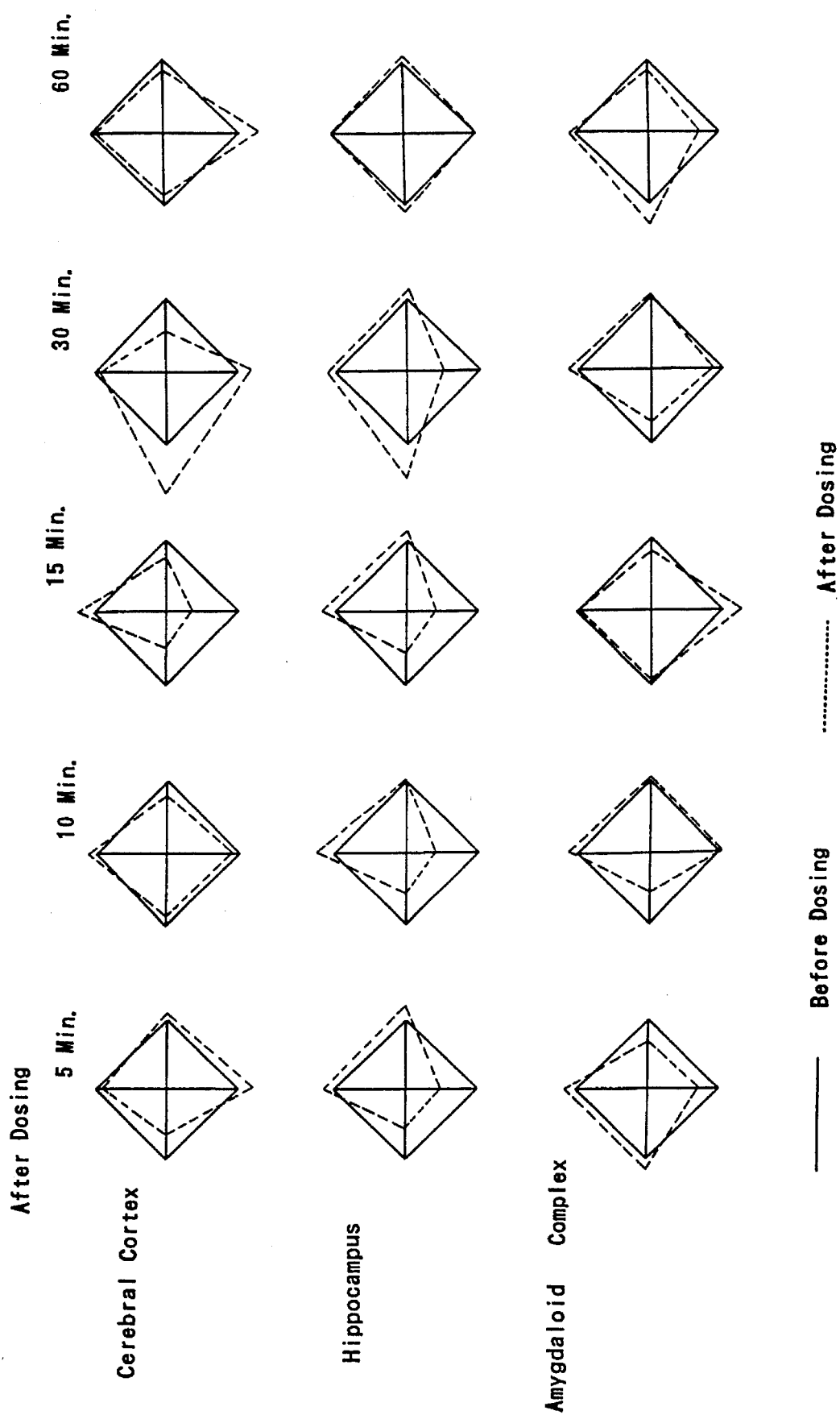
FIG. 1 is a relative drawing showing the changes over time in deep electro-encephalogram of the cerebral cortex, hippocampus and amygdaloid complex in the case of administration of theanine alone.
Figure 2:
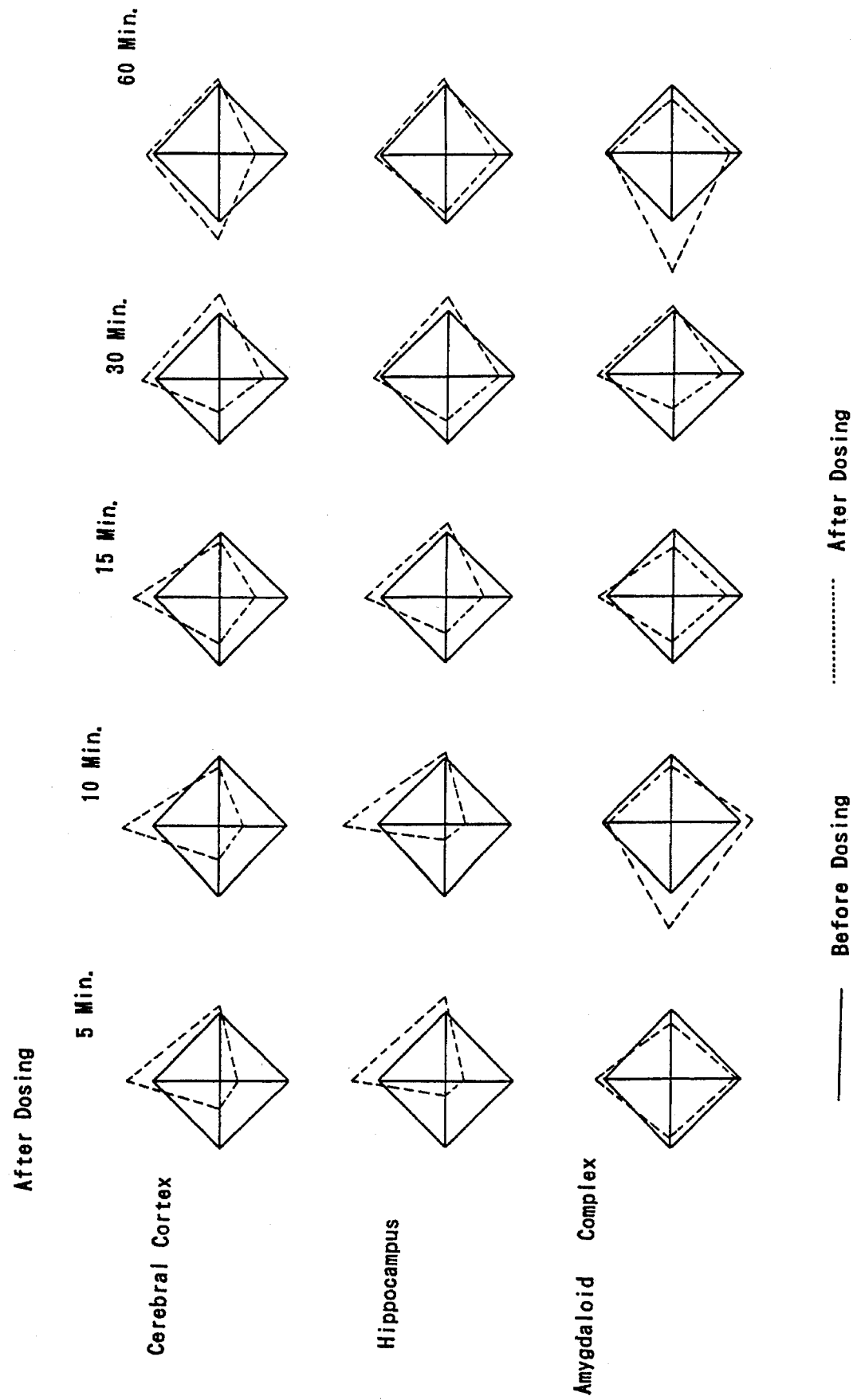
FIG. 2 is a relative drawing showing the changes over time in deep electro-encephalogram of the cerebral cortex, hippocampus and amygdaloid complex in the case of administration of caffeine and theanine.

Although caffeine is contained in tea and coffee, occidentals who prefer coffee are known to be more sensitive to caffeine than orientals who prefer tea. Although racial differences can be considered as the reason for this difference, the inventors of the present invention have proposed a hypothesis that states that it is more reasonable to consider that this difference is due to the presence of substances that inhibit the stimulatory action of caffeine in tea. Thus, breaking away from the conventional way of thinking involving removal of caffeine, the present invention was realized by noticing that, if an existing substance contained in natural substances can be used as a caffeine antagonist, that substance would be extremely useful in allowing even those people who are hypersensitive to caffeine and/or desire to suppress the action of caffeine to consume caffeine-containing beverages or foods without worry over its effects.

Namely, the present invention provides a caffeine stimulation inhibitor, or antagonist, able to be added to caffeine-containing beverages and foods, which is a caffeine stimulation inhibitor having theanine and/or a theanine-containing substance as its active ingredient, wherein said theanine or theanine-containing substance is produced by extraction of tea leaves with a solvent such as water, hot water or ethanol, chemical synthesis, microbial fermentation, plant tissue culturing or other processes.

The above-mentioned theanine may be crude theanine or refined theanine, and the theanine content in the caffeine simulation inhibitor is preferably 10 to no more than 500 times the amount of caffeine ingested.

By refining theanine, frequently contained in caffeine-containing beverages and foods such as tea and coffee, and using it as an active ingredient, in addition to it being able to be used as a harmless additive, by using theanine and/or compositions having theanine as their active ingredient in caffeine-containing beverages and foods, a caffeine stimulation inhibitor can be provided that allows those people who are hypersensitive to caffeine or those people who desire to suppress the action of caffeine (including, but not limited to, those people who desire to drink tea and coffee without impairing sleep) without worry over its effects.

Although the caffeine stimulation inhibitor of the present invention is preferably used as an additive of beverages and foods after processing into liquid, granule or powder form, it may also be individually absorbed in the form of tablets, capsules, granules or syrup.

Experiments and studies were conducted from both behavioral and psychological aspects regarding the antagonistic action of theanine on caffeine, the results of which confirmed said antagonistic action of theanine.

EXAMPLE 1

In order to conduct a study of the behavioral aspects of the antagonistic action of theanine on caffeine, its effects on the amount of spontaneous movement of mice was observed.

1. Animals Used and Grouping

After acclimating 200 six week old, male SPF (specific pathogen free) ICR-JCL mice (purchased from Nippon Clea Co., Ltd.) for a period of 1 week, those healthy animals were selected for use in the study. The animals were assigned to the experimental groups shown below by grouping into 4 groups of 10 animals each so that body weights were uniform. Furthermore, only those animals in which spontaneous movement was previously adapted to be routine behavior were selected for this study in order to determine the amount of spontaneous movement using the rotating cage method.

| Experimental Groups | |
|---|---|
| Group A: | 24.5 ± 0.45 g |
| Group B: | 25.0 ± 0.30 g |
| Group C: | 24.9 ± 0.45 g |
| Group D: | 24.5 ± 0.29 g |

In addition, the animals used in this study were fasted overnight prior to conducting the study.

2. Preparation of Test Substance and Dosing Method

Each of the concentrations of caffeine and theanine were prepared by blending immediately before dosing. Single doses containing 20 ml of the dose preparation per 1 kg of body weight were force fed to each animal using metal gastric tubes.

| Dosing of Test Substance | |
|---|---|
| Group A: | Water (control group) |
| Group B: | Caffeine 4 mg/kg, single dose |
| Group C: | Caffeine 4 mg/kg, theanine 174 mg/kg, mixed dose |
| Group D: | Caffeine 4 mg/kg, theanine 1740 mg/kg, mixed dose |

3. Experimental Method

The number of revolutions for 30 minutes each at 30, 90, 150 and 210 minutes after oral administration of the test substance was determined, and the amount of continuous spontaneous movement was tested using the total number of revolutions in 2 hours according to the rotating cage method.

In addition, organ observations were also made in the form of macroscopic findings after dissection.

4. Experimental Results

The experimental results as determined according to the rotating cage method are shown in Table 1.

Group B demonstrated a clear increase in spontaneous movement due to stimulation, and this level was increased from the early stages of the experiment until conclusion. In contrast, although the amount of spontaneous movement of Group C increased slightly in the early stages of the experiment, this increase was more inhibited than in Group B. Moreover, Group C did not demonstrate an increasing trend, with the amount of spontaneous movement decreasing slightly in the latter half of the experiment. Finally, in Group D, the amount of spontaneous movement was inhibited by more than 20% in comparison with Group B. In addition, there was little difference between this group and the control Group A that was only given water, and changes over time were also similar between these two groups.

EXAMPLE 2

In order to conduct a study of the psychological aspects of the antagonistic action of theanine on caffeine, the effects on the electro-encephalogram of rats were observed.

1. Animals Used and Grouping

Male SD rats (purchased from Japan Charles River Co., Ltd.) having body weights of 500 g were used in this study. The rats were divided into 2 groups of 3 animals each. One group was dosed with theanine alone (Group E), while the other group was dosed with both caffeine and theanine (Group F).

2. Preparation of Test Substance and Dosing Method

The test substances consisting of caffeine and theanine were administered to the rats by intravenous injection.

| Administration of Test Substance | |
|---|---|
| Group E: | Theanine 50 mg/kg, single dose |
| Group F: | Caffeine 4 mg/kg and theanine 50 mg/kg, mixed dose |

3. Experimental Method

Electrodes were implanted in the brains of the rats and the ends of each electrode were brought in contact with the cerebral cortex, hippocampus and amygdaloid complex to prepare deep electrode embedded specimens. The deep electro-encephalogram at each location were then measured with respect to $\alpha$, $\beta$, $\delta$ and $\theta$ waves.

The changes over time were expressed as a relative value with respect to the value at the start of the experiment, assigning a value of 100 to the value of each brain wave at the start of the experiment. Those values were then used to study the effects on electro-encephalogram.

4. Experimental Results

The experimental results in the case of dosing with theanine alone are shown in Table 1, while those in the case of mixed dosing with both caffeine and theanine are shown in Table 2.

Group E tended to demonstrate inhibited stimulation in the cerebral cortex, hippocampus and amygdaloid complex from 5 to 10 minutes after dosing, thus confirming the psychological stabilizing action of theanine. In addition, the cerebral cortex and hippocampus tended to be transiently stimulated 30 minutes later.

Group F clearly tended to demonstrate inhibited stimulation in the cerebral cortex, hippocampus and amygdaloid complex from 5 to 30 minutes after dosing, thus confirming the presence of caffeine stimulation inhibitory action due to the antagonistic action of theanine on caffeine.

TABLE 1

Mouse Behavioral Test Using the Roating Cage Method

| | After 30 minutes | After 90 minutes | After 150 minutes | After 210 minutes | Total No. of Rev. |
|---|---|---|---|---|---|
| Group A | 533.0 ± 20.0 | 572.0 ± 33.1 | 566.6 ± 48.1 | 580.0 ± 47.4 | 2251.6 ± 96.5 |
| Group B | 708.6 ± 40.9 | 799.0 ± 39.6 | 749.3 ± 78.9 | 819.7 ± 78.9 | 3076.6 ± 169.7 |
| Group C | 682.2 ± 33.6 | 733.9 ± 45.8 | 738.3 ± 33.9 | 739.8 ± 41.2 | 2934.2 ± 108.1 |
| Group D | 543.0 ± 24.7 | 621.1 ± 25.1 | 597.7 ± 59.8 | 639.7 ± 51.1 | 2406.3 ± 112.8 |

We claim:

1. A method for inhibiting caffeine stimulation, comprising the step of adding a caffeine stimulation inhibitor containing theanine to foods and beverages, such that said theanine is present in an amount between 10 and 500 times greater than an amount of caffeine present in said foods and beverages.

2. A method for inhibiting caffeine stimulation according to claim 1, wherein said caffeine stimulation inhibitor is in powder form.

3. A method for inhibiting caffeine stimulation according to claim 1, wherein said caffeine stimulation inhibitor is in granular form.

4. A method for inhibiting caffeine stimulation according to claim 1, wherein said caffeine stimulation inhibitor is in liquid form.

5. A method for inhibiting caffeine stimulation according to claim 1, wherein said caffeine stimulation inhibitor is in the form of tablets.

6. A method for inhibiting caffeine stimulation according to claim 1, wherein said caffeine stimulation inhibitor is in the form of capsules.

7. A method for inhibiting caffeine stimulation according to claim 1, wherein said caffeine stimulation inhibitor is in the form of syrup.

8. A method for inhibiting caffeine stimulation according to claim 1, wherein the theanine is extracted from tea leaves.

9. A method for inhibiting caffeine stimulation according to claim 1, wherein the theanine is crude theanine.

10. A method for inhibiting caffeine stimulation according to claim 1, wherein the theanine is raw theanine.

11. A food or beverage product comprising foods or beverages containing caffeine and theanine in an amount between 10 and 500 times greater than the amount of caffeine contained in said foods or beverages.

* * * * *